(12) United States Patent
Brown (10) Patent No.: US 8,480,868 B2
(45) Date of Patent: *Jul. 9, 2013

(54) METHOD FOR DISTINGUISHING ELECTROCHEMICAL SENSORS

(75) Inventor: Daniel V. Brown, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/480,096

(22) Filed: May 24, 2012

(65) Prior Publication Data

US 2012/0228156 A1    Sep. 13, 2012

Related U.S. Application Data

(63) Continuation of application No. 11/989,179, filed as application No. PCT/US2006/030626 on Aug. 4, 2006, now Pat. No. 8,211,292.

(60) Provisional application No. 60/705,903, filed on Aug. 5, 2005.

(51) Int. Cl.
  *G01N 27/26* (2006.01)

(52) U.S. Cl.
  USPC ............... 204/403.04; 205/777.5; 205/792

(58) Field of Classification Search
  USPC .................................................. 205/775
  See application file for complete search history.

(56) References Cited

U.S. PATENT DOCUMENTS

| 5,540,828 | A | 7/1996 | Yacynych |
| 5,856,195 | A | 1/1999 | Charlton |
| 5,980,709 | A | 11/1999 | Hodges et al. |
| 6,284,545 | B1 | 9/2001 | Warburton et al. |
| 6,444,115 | B1 | 9/2002 | Hodges et al. |
| 6,531,040 | B2 | 3/2003 | Musho et al. |
| 6,645,368 | B1 * | 11/2003 | Beaty et al. ............ 205/792 |
| 7,909,983 | B2 | 3/2011 | Popovich et al. |
| 2002/0160517 | A1 | 10/2002 | Modzelewski et al. |

(Continued)

FOREIGN PATENT DOCUMENTS

| EP | 1 447 452 | 8/2004 |
| GB | 2 296 332 | 6/1996 |

(Continued)

OTHER PUBLICATIONS

International Search Report for PCT/US2006/030626 dated Jan. 12, 2007 (4 pages).

(Continued)

*Primary Examiner* — Luan Van
*Assistant Examiner* — Steven Rosenwald
(74) *Attorney, Agent, or Firm* — Nixon Peabody LLP (57) ABSTRACT

A method for distinguishing between types of electrochemical test sensors in a meter is disclosed. The method comprises the acts of providing an electrochemical test sensor comprising an enzyme and a chemical additive, contacting the test sensor to the meter to form an electrical connection, applying a potential having a magnitude sufficient to initiate a redox reaction of the chemical additive, and determining which type of electrochemical test sensor is being used based on whether a predetermined signal has been generated after the potential has been applied. The meter is adapted to determine an analyte concentration in a fluid sample.

23 Claims, 4 Drawing Sheets

U.S. PATENT DOCUMENTS

| | | |
|---|---|---|
| 2003/0032190 A1 | 2/2003 | Brown et al. |
| 2003/0106809 A1 | 6/2003 | Kermani et al. |
| 2003/0138356 A1 | 7/2003 | Gilmour et al. |
| 2005/0161344 A1* | 7/2005 | Kermani et al. ........... 205/777.5 |

FOREIGN PATENT DOCUMENTS

| | | |
|---|---|---|
| JP | 08145944 | 6/1996 |
| JP | 11237364 | 8/1999 |
| JP | 2004/138407 | 5/2004 |
| WO | WO 90/12113 | 10/1990 |
| WO | WO 96/13707 | 5/1996 |
| WO | WO 02/054055 | 7/2002 |
| WO | WO 02/071044 | 9/2002 |
| WO | WO 03/033726 | 4/2003 |
| WO | WO 03/146110 | 8/2003 |
| WO | WO 03/091717 | 11/2003 |
| WO | WO 2004/113911 | 12/2004 |
| WO | WO 2005/045413 | 5/2005 |
| WO | WO 2005/057173 | 6/2005 |

OTHER PUBLICATIONS

European Search Report for EP 09011998.3 dated Nov. 27, 2009 (6 pages).

Hui, Tit-Wah; Wong, Kwok-Yin; Shiu, Kwok-Keung; "Kinetics of o-Benzoquinone Mediated Oxidation of Glucose by Glucose Oxidase at Edge Plane Pyrolytic Graphite Electrode", Electroanalysis, 1996, 8, No. 6, pp. 597-601.

* cited by examiner

METHOD FOR DISTINGUISHING ELECTROCHEMICAL SENSORS

CROSS-REFERENCE TO RELATED APPLICATION

This application is a continuation of U.S. patent application Ser. No. 11/989,179, filed Jan. 22, 2008, which is a U.S. national phase of International Application No. PCT/US2006/030626, filed Aug. 4, 2006, which claims the benefit of priority of U.S. Provisional Application No. 60/705,903, filed on Aug. 5, 2005, all which are incorporated by reference in their entireties.

FIELD OF THE INVENTION

The present invention relates generally to a method for distinguishing electrochemical test sensors, and, more particularly, to a method for distinguishing between multiple versions of electrochemical test sensors that utilizes a chemical marker, or chemical additive, in the test sensor.

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with blood glucose. The testing end of the test sensor is adapted to be placed into the fluid being tested, for example, blood that has accumulated on a person's finger after the finger has been pricked. The fluid is drawn into a capillary channel that extends in the test sensor from the testing end to the reagent material by capillary action so that a sufficient amount of fluid to be tested is drawn into the test sensor. Alternatively, the person could apply a drop of blood to the test sensor that incorporates a reactive zone containing biosensing or reagent material capable of reacting with blood glucose. A voltage is applied, causing the fluid to then chemically react with the reagent material in the test sensor, resulting in an electrical signal indicative of the glucose level in the fluid being tested. This signal is supplied to a sensor-dispensing instrument, or meter, via contact areas located near the rear or contact end of the test sensor and becomes the measured output.

A problem occurs when the test sensor is modified, such as, for example, modifying the reagent material. Modified test sensors are typically newer test sensor versions with improved features, such as improved performance or shortened test times. The modified test sensors may require the meter to apply different calibration information and testing sequences when testing a sample. During the time period before the modified test sensor is to be launched, there exists significant inventory of existing test sensors. Thus, it is desirable that different versions of test sensors may be used interchangeably in a single instrument or meter. Accordingly, the meter should be capable of distinguishing between the various versions of test sensors so that the proper calibration information and testing sequences are applied, and an accurate analyte reading is obtained.

Existing methods for differentiating between different test sensors versions include requiring a user to perform an affirmative act, such as changing a code chip or pressing a button on the meter, to signal to the meter that the test strip is a newer version requiring the application of different calibration information and/or testing sequences. The requirement that a user perform an affirmative act to signal to the meter which type of test sensor is being used allows for the possibility of human error that can adversely affect the analysis of the test results.

It would be desirable to provide a method for distinguishing between multiple versions of an electrochemical test sensor that would minimize or eliminate the user's involvement.

SUMMARY OF THE INVENTION

According to one embodiment of the present invention, a method for distinguishing between types of electrochemical test sensors in a meter is disclosed. The method comprises the acts of providing an electrochemical test sensor comprising an enzyme and a chemical additive, contacting the test sensor to the meter to form an electrical connection, applying a potential having a magnitude sufficient to initiate a redox reaction of the chemical additive, and determining which type of electrochemical test sensor is being used based on whether a predetermined signal has been generated after the potential has been applied. The meter is adapted to determine an analyte concentration in a fluid sample.

According to another embodiment, a method for distinguishing between types of electrochemical test sensors in a meter is disclosed. The method comprises the acts of providing an electrochemical test sensor, contacting the test sensor to the meter to form an electrical connection, applying a potential ranging from an absolute value of about 50 mV to an absolute value of about 350 mV to the test sensor, and determining which type of electrochemical test sensor is being used based on whether a predetermined signal has been generated. The test sensor includes glucose oxidase and a chemical additive. The meter is adapted to determine a glucose concentration in a fluid sample.

According to yet another embodiment, a method for determining the concentration of an analyte in a fluid sample is disclosed. The method comprises the acts of providing an electrochemical test sensor including an enzyme, contacting the test sensor to the meter to form an electrical connection, applying a first potential, determining which type of electrochemical test sensor is being used based on whether a predetermined signal has been generated, applying a test sequence corresponding to the type of electrochemical test sensor, and applying a second potential to initiate a reaction with the analyte so as to assist in determining the analyte concentration of the fluid sample. The meter is adapted to determine an analyte concentration in a fluid sample. The magnitude of the first potential is insufficient to initiate a reaction with the analyte.

The above summary of the present invention is not intended to represent each embodiment or every aspect of the present invention. Additional features and benefits of the present invention are apparent from the detailed description and figures set forth below.

BRIEF DESCRIPTION OF THE DRAWINGS

FIG. 3b is a front view of a sensor-dispensing instrument according to one embodiment that is adapted to receive the cartridge of FIG. 3a.

DESCRIPTION OF ILLUSTRATED EMBODIMENTS

The present invention is directed to a chemical method for distinguishing between multiple versions of an electrochemical test sensor. Electrochemical test sensors are used to determine concentrations of at least one analyte in a fluid. Analytes that may be measured include glucose, lipid profiles (e.g., cholesterol, triglycerides, LDL, and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids such as ISF (interstitial fluid), urine, and non-body fluids. As used within this application, the term "concentration" refers to an analyte concentration, activity (e.g., enzymes and electrolytes), titers (e.g., antibodies), or any other measure of concentration used to measure the desired analyte.

The electrochemical test sensors to be used in determining analyte concentrations are typically provided with a capillary channel that extends from the front or testing end of the test sensors to biosensing or reagent material disposed in the test sensor. The reagent may be stored within the test sensor in a dried ink form to promote an extended shelf life of the test sensor. When the testing end of the test sensor is placed into fluid (e.g., blood that is accumulated on a person's finger after the finger has been pricked), a portion of the fluid is drawn into the capillary channel by capillary action. The fluid then mixes with the reagent material in the test sensor and chemically reacts with the reagent material so that an electrical signal indicative of the analyte (e.g., glucose) level in the fluid being tested is supplied and subsequently transmitted to a sensor-dispensing instrument, or meter.

Figure 1:
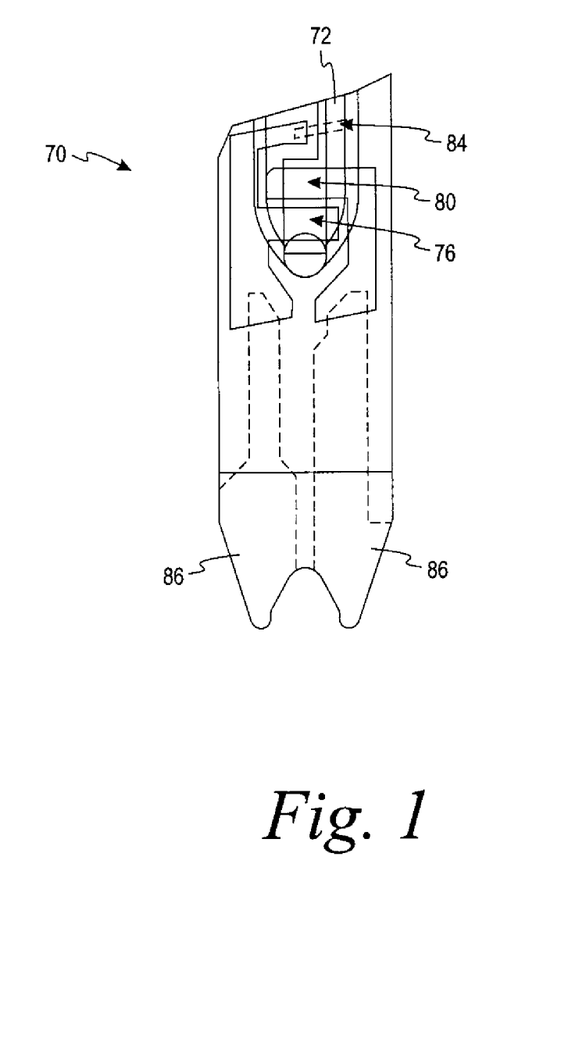
FIG. 1 is a top view of a test sensor according to one embodiment.

One non-limiting example of an electrochemical test sensor is shown in FIG. 1. FIG. 1 depicts a test sensor 70 that includes a capillary channel 72, meter contacts 86, and a plurality of electrodes 76 and 80. The plurality of electrodes includes a working (measuring) electrode 80 and a reference electrode 76. The electrochemical test sensor may also contain at least three electrodes, such as a working electrode, a reference electrode, and an auxiliary or "counter" electrode. The capillary channel 72 contains reagent, as will be discussed in more detail below. Examples of electrochemical test sensors, including their operation, may be found in, for example, U.S. Pat. No. 6,531,040 assigned to Bayer Corporation. It is contemplated that other electrochemical test sensors may be employed.

The electrochemical test sensor 70 also contains an optional trigger electrode 84, as shown in FIG. 1. The trigger electrode 84 is a sub-element of the reference electrode 76. When a fluid sample is placed on the test sensor 70, it first contacts the trigger electrode 84. The working electrode 80 and the reference electrode 76 are located further downstream in terms of the direction of sample fluid flow, relative to the trigger electrode 84. The processor tracks the amount of time it takes for the fluid to travel from the trigger electrode 84 to the working electrode 80 and the reference electrode 76 by determining the electrochemical current time course, which is analyzed by the processor. Based on the current time course, the processor may respond by generating the analyte concentration, such as the concentration of glucose present in the blood sample, or by generating an error code indicating that insufficient blood sample was present in the sensor to make the determination.

Electrochemical test sensors of the type known as biosensors include a biochemical recognition element as a sensor reagent. The sensor reagent may influence items such as the amount of fluid sample needed and the length of time needed to react with the analyte to determine the analyte concentration. The reagent generally comprises active ingredients and support ingredients. One active ingredient generally includes an appropriately selected enzyme to react with the desired analyte or analytes to be tested. For example, when the analyte being tested is glucose, electrochemical test sensors may utilize the enzyme glucose oxidase or glucose dehydrogenase to react with the glucose in the sample. Enzymes used in testing cholesterol concentrations may include, for example, cholesterol oxidase and cholesterol esterase. Another active ingredient generally included in an electrochemical test sensor is a mediator to transfer electrons, such as pyrrolo-quinoline, quinone, glucose dehydrogenase, a ferrocene derivative, (e.g., dimethylferrocene) or a ferricyanide derivative (e.g., potassium ferricyanide, 7,7,8,8-tetracyanoquinodimethane, tetrathiafulvalene, N-methylphenazinium, or cobalt hexamine). Mediators may also be appropriate for testing other types of analytes, such as cholesterol. Stabilizing agents may also be added to the sensor reagent to promote a longer shelf life. The reagent of a test sensor used to measure glucose, as one example, utilizes potassium ferricyanide as a mediator and glucose oxidase to react with the glucose in the sample.

To obtain improved electrochemical test sensor performance, the instrument or meter may be capable of identifying that a new test sensor is being used. New test sensors or new versions of existing test sensors may have different assay protocols or programs associated with different product lot numbers. A new test sensor version may require that the meter apply different test sequences, test times, algorithms, voltage, calibration information, or the like. Calibration information associated with a test sensor is used to compensate for different characteristics of test sensors, which may vary on a lot-to-lot basis. Calibration information may be read by the processor before the fluid sample to be measured is received. Calibration information may be read by the processor after the fluid sample to be measured is received, but not after the concentration of the analyte has been determined. One method of determining an analyte concentration of a fluid sample uses electrical current readings and at least one equation. In this method, equation constants are identified using the calibration information or codes corresponding to the signal generated. These constants may be identified by (a) using an algorithm to calculate the equation constants or (b) retrieving the equation constants from a lookup table for a particular predefined calibration code that is read from the generated signal. Variations of this process will be apparent to those of ordinary skill in the art from the teachings disclosed herein, including but not limited to, the drawings.

According to one method of the present invention, a type or version of an electrochemical test sensor may be determined by a meter itself, requiring minimal user interaction. An electrochemical test sensor is provided that includes an appropriately selected enzyme to react with the desired analyte or analytes to be tested. Additionally, the electrochemical test sensor includes an appropriately selected chemical additive.

The type of chemical additive depends on the type of analyte being tested and is appropriately selected if (1) a redox reaction may occur without the presence of a sample including the analyte and (2) the amount of potential typically required for the reaction to occur is reduced. The electrochemical test sensor is then contacted to a meter, which is adapted to determine the concentration of the analyte in a fluid sample, to form an electrical connection. A reduced first potential is then applied to the electrochemical test sensor. The first potential has a first magnitude such that reduction and oxidation reactions of the chemical additive are initiated. The magnitude of the first potential is lower than the potential required to test the fluid sample. Applying the first potential initiates the redox reaction, which, in turn, generates a signal. This signal is observed by the meter, and the meter then determines which electrochemical test sensor type or version is being used based on the amount of current generated. The meter may then apply the appropriate test sequence to determine the concentration of the analyte in the fluid sample.

In one method, the meter generally applies a potential, which is lower than that typically required to test the analyte, when it is first activated to determine which type of test sensor is in place and which test sequence will need to be applied. The activation step can be initiated by a number of means including a user-operated switch, test sensor insertion, or test sensor presentation from a sensor magazine or cartridge. The meter may then apply this potential every several milliseconds until a current is generated. If an older test sensor is used, which does not incorporate a suitable chemical additive, no reaction will occur because the applied potential is too low. Thus, no current is generated. The meter then determines that an older test sensor is being used, and the corresponding standard test sequence and calibration information are applied. On the other hand, if a new test sensor or test sensor version incorporating a suitable chemical additive is used, the redox reactions occur, and a current is generated and sent to the processor. The processor determines which new test sensor version is being used based on the amount of current generated during the redox reactions. As a result, the processor applies the predefined test sequence corresponding to that test sensor version. Thus, the need for a user to manually change a code chip or press a button corresponding to the test sensor to indicate to the meter which test sensor is being used is eliminated.

For example, a first test sensor may be an existing, older version test sensor that includes a first reagent in which an analyte concentration is determined in a longer time period (e.g., 30 seconds). A user may choose to use a modified, newer test sensor having a second reagent that includes a suitable chemical additive, in which the analyte concentration is determined in a shorter time period (e.g., 5 to 10 seconds). In this method, the meter applies a potential lower than is typically used to test the analyte concentration. The potential is high enough, however, to cause the redox reactions of the chemical additive to occur. A current is subsequently generated, which is observed by the meter. The meter then recognizes that the test sensor being used incorporates the second reagent and determines the glucose concentration in the shorter time period according to the corresponding test sequence.

In one embodiment of the present invention, an electrochemical test sensor for testing glucose in a fluid sample includes a silver salt of ferrocyanide ($Ag_4Fe(CN)_6$) chemical additive. It is contemplated that other chemical additives including, but not limited to, silver carbonate ($Ag_2CO_3$), silver bromate ($AgBrO_3$), iron (III) phenanthroline, butylated hydroxytoluene ($C_{15}H_{24}O$), 1,2-benzoquinone, acetaminophen, and ascorbic acid may be used. By incorporating the silver salt of ferrocyanide, the reduction and oxidation reactions shown in Equations 1 and 2 occur even without the addition of glucose and require only a fraction of the potential applied to test the sample. The reduction reaction, shown in Equation 1, of silver ferrocyanide to silver and ferrocyanide occurs at the counter electrode, serving as a cathode. The oxidation reaction, shown in Equation 2, occurs at the anode, or working electrode.

$$Ag_4Fe(CN)_6 + 4e^- \rightarrow 4Ag + Fe(CN)_6^{4-} \quad 0.194\text{ V vs. NHE} \quad \text{(Equation 1)}$$

$$Fe(CN)_6^{4-} \rightarrow Fe(CN)_6^{3-} + 1e^- \quad -0.460\text{ V vs. NHE} \quad \text{(Equation 2)}$$

A potential ranging from an absolute value of about 50 mV to an absolute value of about 350 mV (from about −50 mV to about −350 mV) is used for the reaction to take place. Alternatively, a potential ranging from an absolute value of about 150 mV to an absolute value of about 250 mV (from about −150 mV to about −250 mV) is used for the reaction to take place. The level of applied potential varies depending upon the pairing of reduction and oxidation reactions, the chemical additive selected, and the electrode material. Examples of electrode materials include, but are not limited to, carbon, gold, palladium, and combinations thereof.

It is also contemplated that the polarity may be reversed. For example, some biosensors utilize ferricyanide as a mediator to accept electrons from the oxidized form of an enzyme. In such a biosensor, it is advantageous that the ferricyanide that has been reduced to ferrocyanide by, for example, contamination or instability, be converted back to ferricyanide. In such a biosensor with polarity reversed during the initial potential application, the working electrode initially supports a reduction reaction while the counter electrode supports an oxidation reaction. If ferrocyanide is present as the additive at the counter electrode, it is oxidized to ferricyanide during the initial potential application. At the same time, the working electrode reduces silver ferrocyanide, silver carbonate, silver bromate, iron phenanthroline, butylated hydroxytoluene, benzoquinone acetaminophen, or ascorbic acid disposed at the working electrode.

The chemical additive may be incorporated into the test sensor in several different ways. Referring back to FIG. 1, according to some embodiments, the chemical additive is incorporated in a separate ink printed on top of the trigger electrode 84, the working electrode 80, or a combination thereof. The ink in these embodiments may be screen printed or microdeposited. In other embodiments, the chemical additive may be a constituent of the trigger electrode ink, the working electrode ink, or the reagent ink. The reagent ink is a separate layer printed on top of the electrodes. The latter embodiments may be more desirable since they do not require an additional manufacturing step. The amount of chemical additive may vary but is generally from about 0.1 to about 10 nanomoles. It is desirable that the amount of silver salt be minimized so that it sends a signal measurable to the instrument and is consumed shortly thereafter.

According to one method of determining the glucose level of a fluid sample, the sample is placed on the electrochemical test sensor, which includes a potassium ferricyanide mediator and a glucose oxidase enzyme. The glucose in the fluid sample reacts with the glucose oxidase to make gluconic acid and the reduced form of glucose oxidase. The reduced glucose oxidase then reacts with ferricyanide to make ferrocyanide. The ferrocyanide is then oxidized at the working electrode, acting as an anode, by the meter applying, for example, approximately +400 mV potential relative to the counter electrode. The oxidation reaction generates a current that is directly proportional to the concentration of glucose in the sample. An electrical assembly within the meter then converts the amount of current generated into a corresponding glucose concentration reading.

Figure 2:
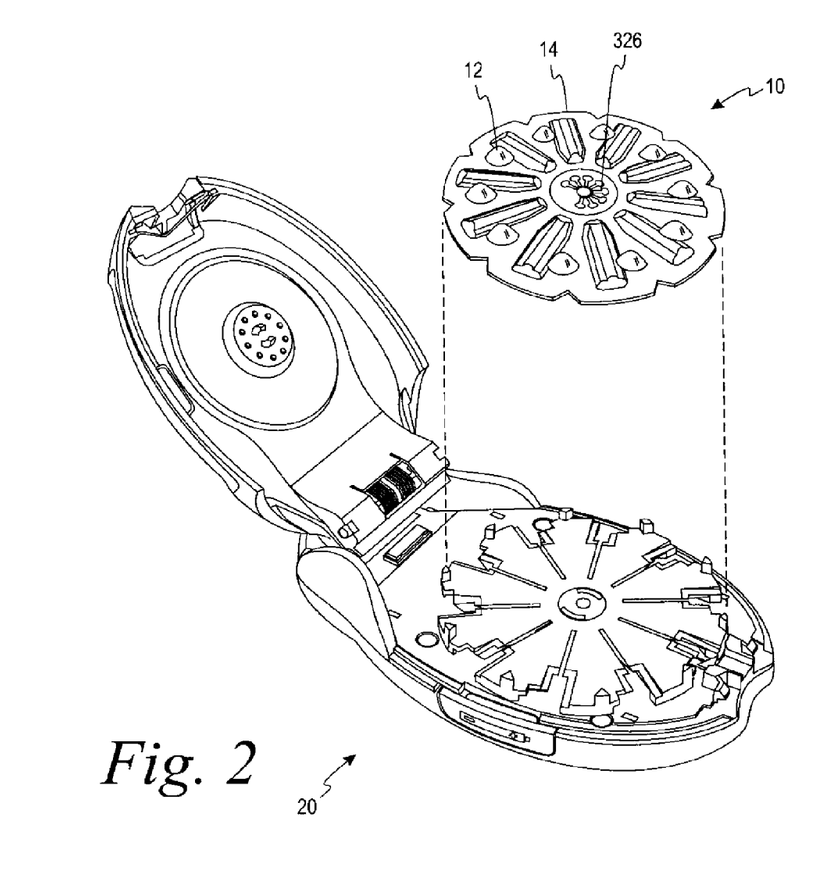
FIG. 2 is a perspective view of a sensor-dispensing instrument or meter in the open position showing a sensor pack being inserted according to one embodiment.

A sensor-dispensing instrument, or meter, in one embodiment uses a test sensor adapted to receive a fluid sample to be analyzed. Such a meter 20 is shown in FIG. 2. An electrochemical test sensor contacts the meter 20 such that an electronic connection is established. The meter 20 also contains a processor (not shown) adapted to perform a predefined test sequence for measuring a predefined parameter value. The processor is encoded with calibration information, codes, and/or test sequences assigned for use in the clinical value computations corresponding to each test sensor version. A memory is coupled to the processor for storing predefined parameter data values.

A plurality of electrochemical test sensors is typically stored in a disposable cartridge. For example, the plurality of test sensors may be stored in a test-sensor pack where the test sensors are individually packaged in sensor cavities (i.e., a blister-type pack). An example of a disposable cartridge 10 being placed in the meter 20 is depicted in FIG. 2. The disposable cartridge 10 is an example of a blister-type pack. The cartridge 10 includes a plurality of electrochemical test sensors 12 that is individually stored in a respective one of a plurality of sensor cavities 14. The cartridge 10 is generally circular in shape with the sensor cavities 14 extending from near the outer peripheral edge toward and spaced apart from the center of the cartridge 10. It is contemplated, however, that other sensor packs may be of different shapes than that depicted in FIG. 2. For example, the sensor package may be a square, a rectangle, another polygonal shape, or a non-polygonal shape, including oval. The disposable cartridge 10 of FIG. 2 is further described at U.S. Publication No. 2003/0032190 that published on Feb. 13, 2003 and is entitled "Mechanical Mechanism for a Blood Glucose Sensor-Dispensing Instrument." In this embodiment, each sensor cavity 14 accommodates one of the plurality of test sensors 12.

Figure 3A:
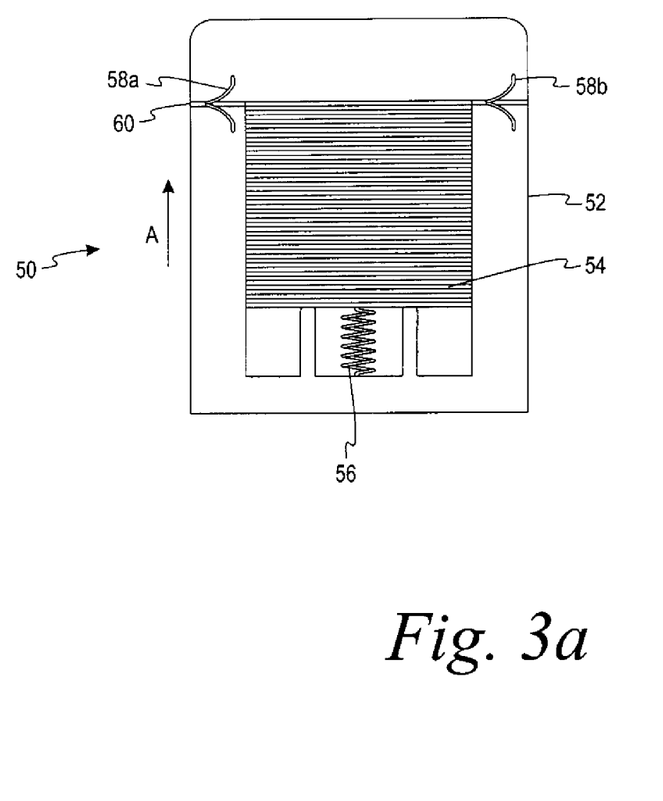
FIG. 3a is a front view of a disposable cartridge with a plurality of stacked test sensors according to one embodiment.
Figure 3B:
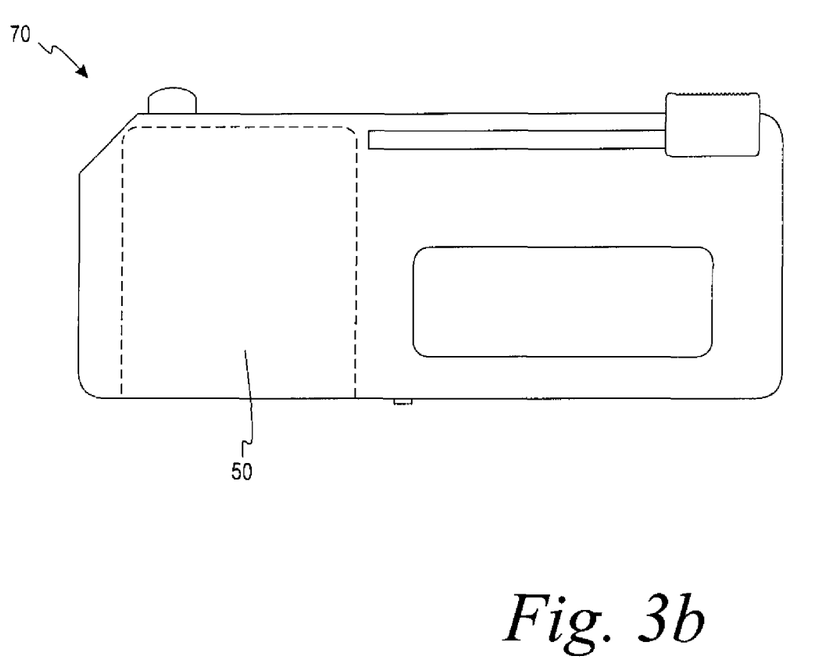

The plurality of test sensors may be stacked in a disposable cartridge such as shown in FIG. 3a. Referring to FIG. 3a, a disposable cartridge 50 includes a housing 52 and a plurality of stacked electrochemical test sensors 54 that is moved in the direction of arrow A via a spring 56. The cartridge 50 also includes a plurality of seals 58a,b that protects the stacked test sensors 54 from humidity. The test sensors 54, one at a time, exit the cartridge 50, via an opening 60. The disposable cartridge 50 may be stored in an instrument or meter 70 of FIG. 3b. It is contemplated that other cartridges besides cartridges 10, 50 may be used. It is contemplated that the electrochemical test sensors may be used with other instruments or meters than instruments 10 and 70 depicted in FIGS. 2, 3b. The electrochemical test sensors may also be used in other types of sensor packs than sensor package 12. For example, the electrochemical test sensors may be used in sensor packages such as a drum-type sensor package.

Because of the limited shelf life of many test sensors, the cartridges 10, 50 of FIGS. 2 and 3a may vary in the number of electrochemical test sensors that are included so as to address the needs of different users. Typically, the cartridges contain from about 10 to about 100 test sensors and, more specifically, contain from about 25 to about 50 test sensors.

Alternative Process A

A method for distinguishing between types of electrochemical test sensors in a meter, the method comprising the acts of:

providing an electrochemical test sensor comprising an enzyme and a chemical additive;

contacting the test sensor to the meter to form an electrical connection, the meter being adapted to determine an analyte concentration in a fluid sample;

applying a potential having a magnitude sufficient to initiate a redox reaction of the chemical additive; and determining which type of electrochemical test sensor is being used based on whether a predetermined signal has been generated after the potential has been applied.

Alternative Process B

The method of Alternative Process A further comprising the act of matching the predetermined signal to a corresponding test sequence.

Alternative Process C

The method of Alternative Process A wherein the act of applying the potential occurs when the meter is activated.

Alternative Process D

The method of Alternative Process A wherein the electrochemical test sensor has a working electrode and a reference electrode.

Alternative Process E

The method of Alternative Process A wherein the electrochemical test sensor has at least three electrodes.

Alternative Process F

The method of Alternative Process A wherein the analyte is cholesterol.

Alternative Process G

The method of Alternative Process A wherein the analyte is glucose.

Alternative Process H

The method of Alternative Process G wherein the chemical additive is selected from the group consisting of silver ferrocyanide ($Ag_4Fe(CN)_6$), silver carbonate ($Ag_2CO_3$), silver bromate ($AgBrO_3$), iron (III) phenanthroline, butylated hydroxytoluene, 1,2-benzoquinone, acetaminophen, and ascorbic acid.

Alternative Process I

The method of Alternative Process G wherein the enzyme is glucose oxidase.

Alternative Process J

The method of Alternative Process I wherein the absolute values of the potential ranges from about 50 mV to about 350 mV.

Alternative Process K

The method of Alternative Process I wherein the absolute value of the potential ranges from about 150 mV to about 250 mV.

Alternative Process L

A method for distinguishing between types of electrochemical test sensors in a meter, the method comprising the acts of:

providing an electrochemical test sensor, the test sensor including glucose oxidase and a chemical additive;

contacting the test sensor to the meter to form an electrical connection, the meter being adapted to determine a glucose concentration in a fluid sample;

applying a potential ranging from an absolute value of about 50 mV to an absolute value of about 350 mV to the test sensor; and determining which type of electrochemical test sensor is being used based on whether a predetermined signal has been generated.

Alternative Process M

The method of Alternative Process L further comprising the act of matching the predetermined signal to a corresponding test sequence.

Alternative Process N

The method of Alternative Process L wherein the act of applying the potential occurs when the meter is activated.

Alternative Process O

The method of Alternative Process L wherein the chemical additive is selected from the group consisting of silver ferrocyanide ($Ag_4Fe(CN)_6$), silver carbonate ($Ag_2CO_3$), silver bromate ($AgBrO_3$), iron (III) phenanthroline, butylated hydroxytoluene, 1,2-benzoquinone, acetaminophen, and ascorbic acid.

Alternative Process P

The method of Alternative Process L wherein the potential ranges from an absolute value of about 50 mV to an absolute value of about 350 mV.

Alternative Process Q

The method of Alternative Process L wherein the potential ranges from an absolute value of about 150 mV to an absolute value of about 250 mV.

Alternative Process R

A method for determining the concentration of an analyte in a fluid sample, the method comprising the acts of:

providing an electrochemical test sensor including an enzyme;

contacting the test sensor to the meter to form an electrical connection, the meter being adapted to determine an analyte concentration in a fluid sample;

applying a first potential;

determining which type of electrochemical test sensor is being used based on whether a predetermined signal has been generated;

applying a test sequence corresponding to the type of electrochemical test sensor; and applying a second potential to initiate a reaction with the analyte so as to assist in determining the analyte concentration of the fluid sample, wherein the magnitude of the first potential is insufficient to initiate a reaction with the analyte.

Alternative Process S

The method of Alternative Process R wherein the act of determining which type of electrochemical sensor is being used is based on an absence of the predetermined signal.

Alternative Process T

The method of Alternative Process R wherein the analyte is cholesterol.

Alternative Process U

The method of Alternative Process R wherein the analyte is glucose.

Alternative Process V

The method of Alternative Process R wherein act of applying a test sequence includes applying calibration information.

Alternative Process W

The method of Alternative Process R wherein the electrochemical test sensor includes a chemical additive.

Alternative Process X

The method of Alternative Process R wherein the analyte is glucose and the chemical additive is selected from the group consisting of silver ferrocyanide ($Ag_4Fe(CN)_6$), silver carbonate ($Ag_2CO_3$), silver bromate ($AgBrO_3$), iron (III) phenanthroline, butylated hydroxytoluene, 1,2-benzoquinone, acetaminophen, and ascorbic acid.

Alternative Process Y

The method of Alternative Process R wherein the first potential ranges from an absolute value of about 50 mV to an absolute value of about 350 mV.

Alternative Process Z

The method of Alternative Process R wherein the potential ranges from an absolute value of about 150 mV to an absolute value of about 250 mV.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A method of determining a type of electrochemical test sensor used with an instrument configured to be used in determining at least one analyte concentration in a fluid sample, the method comprising the acts of:

forming an electrical connection between an electrochemical test sensor and the instrument, the electrochemical test sensor including an enzyme and a chemical marker;

applying a potential having a magnitude sufficient to initiate a redox reaction of the chemical marker and insufficient to determine the at least one analyte concentration, the potential being applied by the instrument; and determining the type of electrochemical test sensor based on a predetermined amount of current generated in response to the potential being applied.

2. The method of claim 1, wherein the act of applying the potential occurs when the instrument is activated.

3. The method of claim 1, wherein the electrochemical test sensor includes a working electrode and a counter electrode.

4. The method of claim 1, wherein the analyte is glucose.

5. The method of claim 4, wherein the chemical marker is silver ferrocyanide ($Ag_4Fe(CN)_6$), silver carbonate ($Ag_2CO_3$), silver bromate ($AgBrO_3$), iron (III) phenanthroline, butylated hydroxytoluene, 1,2-benzoquinone, acetaminophen, or ascorbic acid.

6. The method of claim 4, wherein the enzyme is glucose oxidase.

7. The method of claim 6, wherein the absolute value of the potential ranges from about 50 mV to about 350 mV.

8. The method of claim 6, wherein the absolute value of the potential ranges from about 150 mV to about 250 mV.

9. The method of claim 1, wherein the act of determining the type of electrochemical test sensor is based on an absence of current generated in response to the potential being applied.

10. A method for determining at least one analyte concentration in a fluid sample, the method comprising the acts of:

activating the instrument to apply a potential to the electrochemical test sensor, the electrochemical test sensor including an enzyme and a chemical marker;

applying the potential to the electrochemical test sensor to generate a predetermined amount of current, the potential having a magnitude sufficient to initiate a redox reaction of the chemical marker and insufficient to determine the at least one analyte concentration, the potential being applied by the instrument;

determining a test sequence associated with the electrochemical test sensor based on a predetermined amount of current generated in response to the potential being applied; and applying the test sequence, the test sequence being used to determine the at least one analyte concentration.

11. The method of claim 10, wherein the act of activating the instrument is initiated via a user-operated switch or insertion of the electrochemical test sensor into the instrument.

12. The method of claim 10, wherein the potential is applied a predetermined number of times or until the predetermined signal is generated.

13. The method of claim 10, wherein the analyte is glucose.

14. The method of claim 13, wherein the enzyme is glucose oxidase.

15. The method of claim 14, wherein the chemical marker is silver ferrocyanide ($Ag_4Fe(CN)_6$), silver carbonate ($Ag_2CO_3$), silver bromate ($AgBrO_3$), iron (III) phenanthroline, butylated hydroxytoluene, 1,2-benzoquinone, acetaminophen, or ascorbic acid.

16. The method of claim 14, wherein the potential ranges from an absolute value of about 50 mV to an absolute value of about 350 mV.

17. The method of claim 14, wherein the potential ranges from an absolute value of about 150 mV to an absolute value of about 250 mV.

18. A method for determining a type of electrochemical test sensor used in a meter, the electrochemical test sensor being configured to be used in determining the concentration of an analyte in a fluid sample, the method comprising the acts of:
   contacting the electrochemical test sensor to an instrument to form an electrical connection, the electrochemical test sensor including an enzyme and a chemical marker, the instrument being adapted to determine an analyte concentration in a fluid sample;
   applying a potential having a magnitude sufficient to initiate a redox reaction of the chemical marker and insufficient to determine the concentration of the analyte, the potential being applied by the instrument;
   determining which type of electrochemical test sensor is being used based on whether a predetermined amount of current is generated in response to the potential being applied, the predetermined amount of current resulting from a redox reaction of said chemical marker included in the electrochemical test sensor; and
   applying a test sequence corresponding to the determined electrochemical test sensor type.

19. The method of claim 18, wherein the act of determining which type of electrochemical test sensor is being used is based on an absence of the predetermined signal.

20. The method of claim 18, wherein the act of determining which type of electrochemical test sensor is being used is based on an amount of the predetermined signal generated.

21. The method of claim 18, wherein the analyte is glucose.

22. The method of claim 21, wherein the chemical marker is silver ferrocyanide ($Ag_4Fe(CN)_6$), silver carbonate ($Ag_2CO_3$), silver bromate ($AgBrO_3$), iron (III) phenanthroline, butylated hydroxytoluene, 1,2-benzoquinone, acetaminophen, or ascorbic acid.

23. The method of claim 22, wherein the first potential ranges from an absolute value of about 50 mV to an absolute value of about 350 mV.

* * * * *